US008672685B2

(12) United States Patent (10) Patent No.: US 8,672,685 B2
Doherty (45) Date of Patent: Mar. 18, 2014

(54) ELECTRON CONFIGURATION TEACHING SYSTEMS AND METHODS

(75) Inventor: David Colby Doherty, Minnetonka, MN (US)

(73) Assignee: Bitwixt Software Systems LLC, Minnetonka, MN (US)

( * ) Notice: Subject to any disclaimer, the term of this patent is extended or adjusted under 35 U.S.C. 154(b) by 741 days.

(21) Appl. No.: 12/574,933

(22) Filed: Oct. 7, 2009

(65) Prior Publication Data

US 2011/0081637 A1 Apr. 7, 2011

(51) Int. Cl.
G09B 23/06 (2006.01)
(52) U.S. Cl.
USPC .......................................... 434/281; 434/278
(58) Field of Classification Search
USPC ................................................. 434/278, 281
See application file for complete search history.

(56) References Cited

U.S. PATENT DOCUMENTS

| | | | | |
|---|---|---|---|---|
| 5,386,507 A | * | 1/1995 | Teig et al. ...................... | 715/836 |
| 5,634,017 A | * | 5/1997 | Mohanty et al. .............. | 715/803 |
| 7,188,055 B2 | * | 3/2007 | Agrafiotis et al. ................ | 703/2 |
| 2007/0198199 A1 | * | 8/2007 | Mills .............................. | 702/32 |
| 2010/0218078 A1 | * | 8/2010 | Channon ....................... | 715/205 |

OTHER PUBLICATIONS

"AutoCAD Tutorial," Mar. 24, 2009 (http://web.archive.org/web/20090324125855/http://autocadlayers.weebly.com/).*
"Atoms and Molecules" Sep. 21, 2007 (http://web.archive.org/web/20070921192809/http://www.biologie.uni-hamburg.de/b-online/library/onlinebio/BioBookCHEM1.html).*
"D orbitals", Jun. 30, 2006 (http://en.wikipedia.org/wiki/File:D_orbitals.svg).*
Applet: Electron Configurations, Bauer, W., Java Applet, © 1999, 1 page.
The ChemCollective: Periodic Table Applet, NSDL Carnegie Mellon, Sep. 24, 2007, 1 page.
Real-Time Visualization of Quantum Atomic Orbitals, Dauger Research, Inc., © Copyright 2001-2008, 4 pages.
David's Whizzy Periodic Table, accessed on Dec. 11, 2009, accessed at http://www.colorado.edu/physics/2000/applets/a3.html, 1 page.
Vining, William J., "Discovery Learning using Chemland Simulation Software," vol. 5, No. 1, Feb. 2000, SpringerLink, 2 pages.
ElectronConfiguration.der, example screen from http://people.okanagon.bc.ca/cdoige/chemland/ElectronConfiguration.htm, accessed on Dec. 11, 2009, 1 page.
ElectronConfiguration 1, accessed on Dec. 11, 2009, accessed at: http://www.explorelearning.com/index.cfm?method=cResource.dspDetail&ResourceID= ... , 2 pages.

(Continued)

Primary Examiner — Xuan Thai
Assistant Examiner — Michael Grant
(74) Attorney, Agent, or Firm — Merchant & Gould P.C.

(57) ABSTRACT

A computerized method and system for demonstrating and teaching electron configurations in atomic structure are disclosed. One method includes presenting to a user one or more user interfaces stored in memory of the computing system, the one or more user interfaces includes a plurality of electron configuration diagrams. The method also includes receiving user input into an orbital box diagram displayed in the one or more user interfaces, the user input defining a possible electron configuration. The method further includes in response to the user input, updating the one or more user interfaces to illustrate the electron configuration received from the user, and if instructed by the user, generates a report regarding the compliance of the user-entered electron configuration with one or more electron configuration rules.

14 Claims, 15 Drawing Sheets

(56) References Cited

OTHER PUBLICATIONS

Electron Configurations, CHEMystery: Atomic Structure and Bonding, accessed on Dec. 11, 2009, accessed at: http://library.thinkquest.org/3659/structures/electronconfig.html, 2 pages.

Example Screens accessed at: http://www.explorelearning.com/index.cfm?method=cResource.dspView&ResourceID=513, accessed on Dec. 11, 2009, 2 pages.

Student Exploration: Electron Configuration, Explore Learning, accessed on Dec. 11, 2009, 7 pages.

Dr. Gutow's Atomic Orbital Viewer, Apr. 2006, 2 pages.

Norton 1, "Electrons and Electromagnetic Radiation," W.W. Norton & Company, © 2003, 4 pages.

Norton 2, "Electron Configuration," accessed on Dec. 11, 2009, accessed at: http://www.wwnorton.com/college/chemistry/gilbert/tutorials/interface.asp?chapter=chapter_03&folder=orbital_filling, 1 page.

Orbital Viewer, Sep. 14, 2004, 2 pages.

Orbital Viewer 2, Grand Orbital Table, Manthey, accessed Dec. 11, 2009, accessed at: http://www.orbitals.com/orb/orbtable.htm, 27 pages.

Shapes of Atomic Orbitals, CHEMystery: Atomic Structure and Bonding, accessed on Dec. 11, 2009, accessed at: http://library.thinkquest.org/3659/structures/shapes.html, 1 page.

Zumdahl, Steven S., "Chemistry," © 1986 by D.C. Heath and Company, 13 pages.

* cited by examiner

ELECTRON CONFIGURATION TEACHING SYSTEMS AND METHODS

BACKGROUND

Atomic structure is typically taught as a part of a high school or college chemistry curriculum. Lessons included in that curriculum often cover information about electron configurations, including atomic orbitals, valence electrons, and various rules used to determine the positions and energy levels of those electrons. In existing curricula, these lessons are provided in textbooks, which include a number of exercises that require students to draw orbital box diagrams and atomic orbitals, and to determine valid electron configurations that will not violate a number of rules (e.g., the Pauli Exclusion Principle, Hund's Rule, and the Aufbau principle).

It can be difficult for students to visualize and make connections between a number of aspects of electron configurations, such as how atomic orbitals fit together in three-dimensional space, the relationship between an element's electron configuration and its position in the periodic table, and the relationships between electron configuration, atomic orbitals, and valence electrons (e.g., as illustrated in electron dot diagrams). Students must manually draw each of these diagrams and may have a difficult time both visualizing the correct configuration and determining when their diagrammed configuration is correct or incorrect.

SUMMARY

In accordance with the following disclosure, the above and other problems are solved by:

In a first aspect, a computerized method for visually demonstrating and teaching electron configuration in an atomic structure is disclosed. The method includes presenting to a user one or more user interfaces stored in memory of the computing system, the one or more user interfaces including a plurality of representations of an atom's electron configuration (electron configuration diagrams). The method also includes receiving user input into an orbital box diagram displayed in the one or more user interfaces, the user input defining a possible electron configuration. The method further includes in response to the user input, updating the one or more user interfaces to illustrate the electron configuration received from the user.

In a second aspect, an electron configuration teaching system includes a display, a memory, and a programmable circuit. The memory is configured to store a plurality of user interfaces capable of presentation on the display, the plurality of user interfaces that implement a plurality of electron configuration diagrams. The programmable circuit is operatively connected to the display and the memory and is configured to execute program instructions to present on the display one or more of the user interfaces. The programmable circuit is further configured to execute program instructions to receive user input into an orbital box diagram displayed in the one or more user interfaces, the user input defining a possible electron configuration, and to update the one or more user interfaces to illustrate the electron configuration received from the user.

In a third aspect, a computerized method of demonstrating electron configuration in an atomic structure includes presenting to a user one or more user interfaces stored in memory of the computing system, the one or more user interfaces including a plurality of electron configuration diagrams including an atomic orbital simulation, an electron dot diagram, a periodic table, an alphanumeric representation, and an orbital box diagram. The computerized method also includes receiving user input into the orbital box diagram defining a possible electron configuration, and, in response to the user input, updating the one or more user interfaces to illustrate the electron configuration received from the user. The computerized method further includes, upon user request, generating a report regarding compliance of the user-entered electron configuration with one or more electron configuration rules.

DETAILED DESCRIPTION

Figure 1:
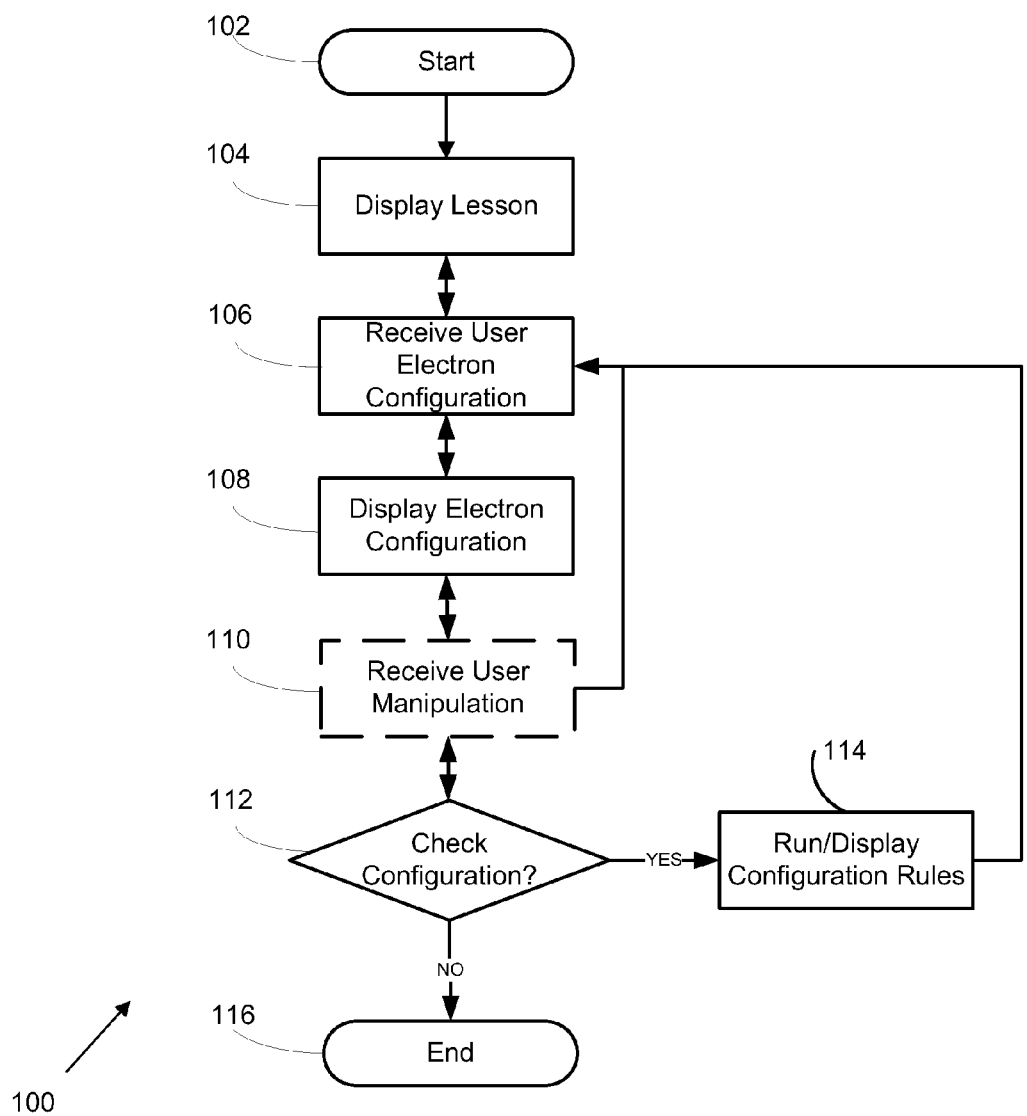
FIG. 1 is a flowchart of methods and systems for computerized modeling of electron configurations, according to certain embodiments of the present disclosure.

Various embodiments of the present disclosure will be described in detail with reference to the drawings, wherein like reference numerals represent like parts and assemblies throughout the several views. Reference to various embodiments does not limit the scope of the disclosure. Additionally, any examples set forth in this specification are not intended to be limiting and merely set forth some of the many possible embodiments related to the disclosure herein.

The logical operations of the various embodiments of the disclosure described herein are implemented as: (1) a sequence of computer implemented steps, operations, or procedures running on a programmable circuit within a computer, and/or (2) a sequence of computer implemented steps, operations, or procedures running on a programmable circuit within a directory system, database, or compiler.

In general the present disclosure relates to methods and systems for demonstrating and teaching electron configuration in an atomic structure. In particular, the present disclosure relates to computerized, interactive electron configuration diagrams that illustrate the connections between various concepts of atomic structure and simulate atomic orbitals, based on input electron configurations, and optionally checks input electron configurations for violations of electron configuration rules. This demonstration and teaching system can be incorporated, for example, into any of a number of types of computerized lessons or generalized curricula.

Referring now to FIG. 1, a flowchart 100 of methods and systems for computerized modeling of electron configurations are shown, according to certain embodiments of the present disclosure. The methods and systems illustrated by flowchart 100 can be executed on a computer, such as the one described below in conjunction with FIG. 2, or can be hosted at a server computer, with the various user interfaces described herein communicated to a remote system. The displayed user interfaces are in either instance used by teachers or students or others having interest in the curriculum (collectively "users").

The flowchart 100 is instantiated at a start operation 102, which corresponds to initializing software on a computing system, for example by selecting software or a lesson within such software (see FIG. 8) that causes initialization of the electron configuration demonstration software.

Operational flow proceeds to a display lesson module 104, which displays a lesson associated with atomic structure and electron configuration. The lesson can include, for example, textual or graphical demonstrations of manipulation of electron configurations in orbital box diagrams and illustrations of various electron distributions among atomic orbitals, and rules related thereto.

Figure 8:
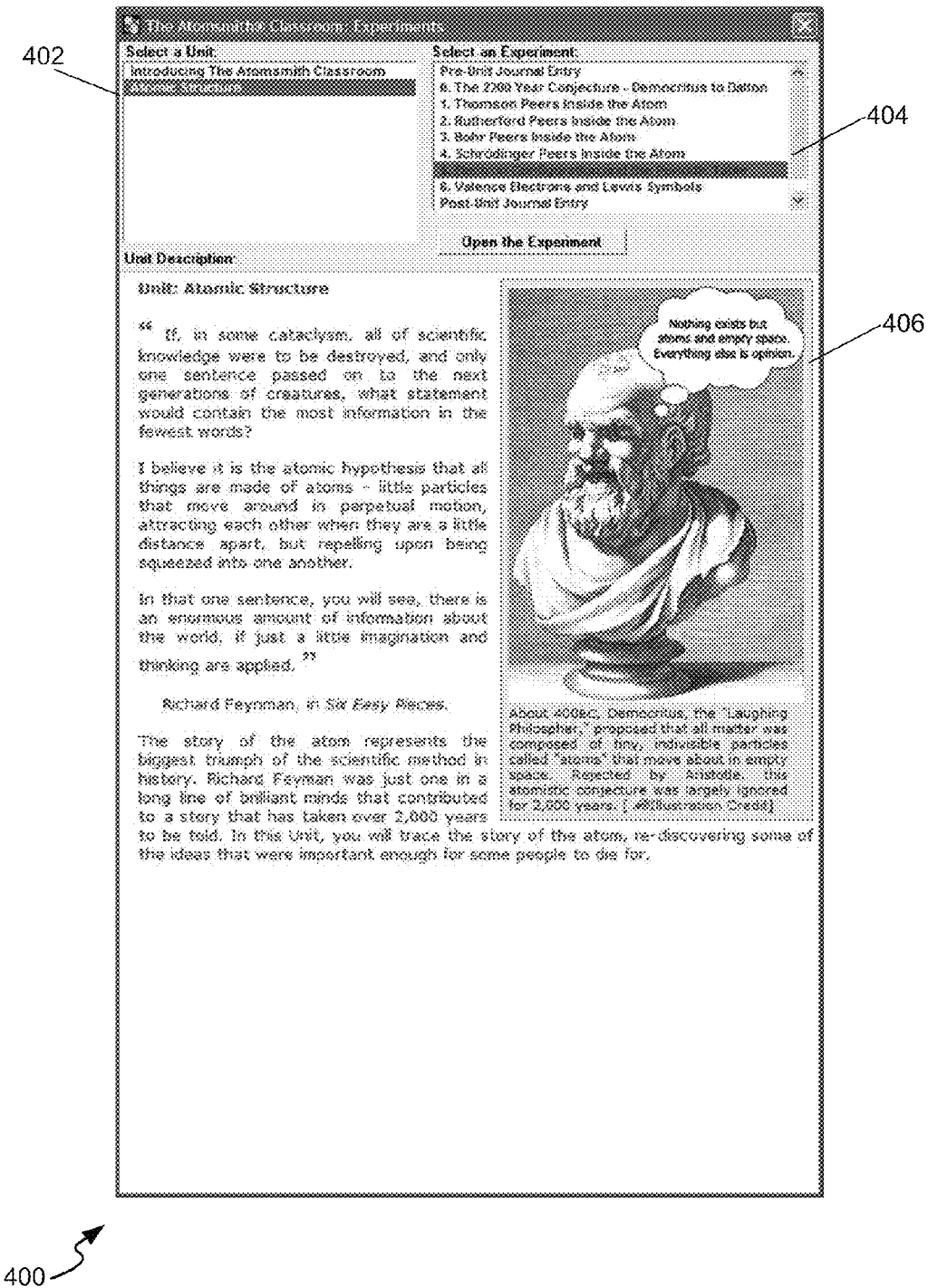
FIG. 8 illustrates an example interface for an online lesson.

One example of such a lesson is shown in FIG. 8. A user interface 400 includes a unit module 402 that allows the users to select a unit for the lesson, and an experiment module that allows the users to select an experiment associated with the selected unit. A description module 406 provides a description related to the selected unit and/or experiment.

In example embodiments described herein, the modeling of electron configurations is provided in conjunction with the online lesson. In other examples, the modeling can be provided in conjunction with a written lesson. In yet other examples, the modeling can be provided separate from any lesson or in conjunction with other curricula. Other configurations are possible.

Figure 3A:
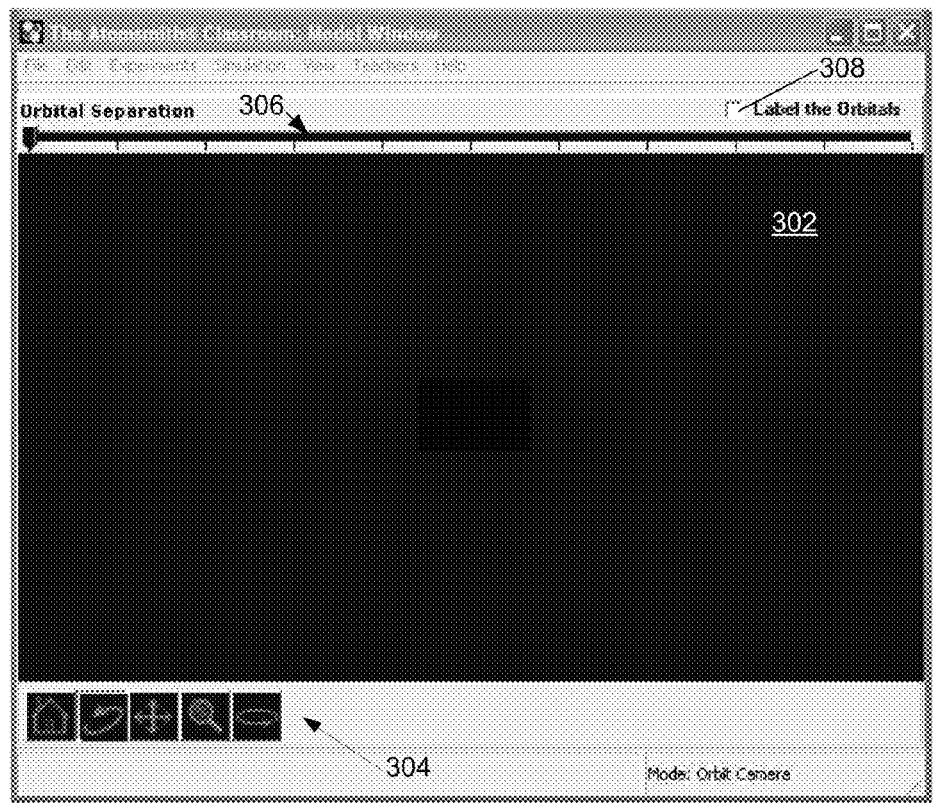
FIG. 3A illustrates a user interface capable of displaying an atomic orbital simulation that represents the spatial distribution of an electron in an atom, according to possible embodiments of the present disclosure.
Figure 3B:
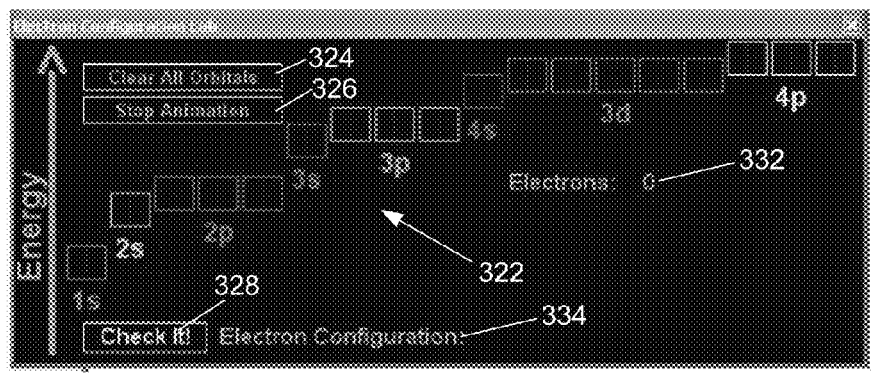
FIG. 3B illustrates a user interface for user-manipulation of a model of electron configurations in an atom, according to possible embodiments of the present disclosure.

Referring again to FIG. 1, the display lesson module 104 includes generation of one or more user interfaces that are configured to be presented on display user interfaces, at least one of which includes an electron configuration diagram. The electron configuration diagram can take any of a number of forms. In certain embodiments, the electron configuration diagram includes a simulated atom including various atomic orbitals, e.g., s, p, d, and f atomic orbitals. Other electron configuration diagrams (e.g., electron dot diagrams, alphanumeric representations, schematic diagrams, a periodic table, or other types of diagrams) could be used as well. One example diagram and associated user interface for entering user electron configurations is shown in FIGS. 3A-3B, described below.

A user electron configuration module 106 receives user input regarding a possible electron configuration at the computing system that executes or communicates data related to the methods and systems described herein. The user electron configuration module 106 can, in certain embodiments, receive the electron configuration from a user by receiving selection of particular boxes in an orbital box diagram, allowing the user to select the particular orbital, pair, and spin for each individual electron. Example user electron configurations are shown in FIGS. 4B, 5B, 6B, and 7B, below.

A display module 108 presents one or more of the user interfaces displayed to a user to reflect the particular electron configuration selected by the user. In certain embodiments, the display module can update existing user interface features to reflect a particular received electron configuration. In other embodiments, the display module 108 creates new user interfaces, such as a periodic table and an electron dot diagram of the atom reflected by the electron configuration. Example user electron configuration displays and representations of electron configurations are shown in FIGS. 4A, 4B, 5A, 5B, 6A, 6B, 7A, and 7B, below.

A user manipulation module 110 allows user manipulation of one or more of the various user interfaces displaying the electron configuration. As compared to the user electron configuration module 106, the user manipulation module 110 accepts manipulation of one or more of the graphical user interfaces, rather than modification of the current electron configuration. For example, the user manipulation module 110 can receive information relating to electron animation, separation of atomic orbitals, rotation of a simulated atom, movement or pivoting of the simulated atom, labeling of orbitals, or other view modification operations. Example graphical modifications are shown in FIGS. 7A, 7B, 7D, and 7E, described below.

An electron configuration check operation 112 receives user selection of an electron configuration check option in a user interface (e.g., as described below in conjunction with user interface 3B). If the electron configuration check operation is selected, operational flow branches "yes" and proceeds to a configuration rules module 114.

The electron configuration rules module 114 determines, based on the electron configuration provided by the user into the receive user electron configuration module 106, whether any electron configuration rules are violated. In certain embodiments described herein, three rules that are tested include the Pauli Exclusion Principle, Hund's Rule, and the Aufbau principle.

The Aufbau Principle requires that all electrons occupy atomic orbitals of the lowest energy level available. For example, if the 1s orbital remains open, the next electron added to an atom will join that orbital. If the 1s orbital is full (contains two electrons), the next electron will then reside in the 2s orbital. If the 2s orbital is full (contains two electrons), the next added electron will reside in a 2p orbital, and so on.

Hund's rule requires that, within each energy level, each orbital receives a single electron before each orbital receives its pair of electrons that can reside in that orbital. For example, in the three 2p orbitals available, each orbital will obtain a single electron before any one orbital obtains a second electron. In addition, the spins of each of these unpaired electrons must be the same.

The Pauli Exclusion Principle requires that, within each orbital, one electron will have "up" spin, while the other electron has "down" spin.

The configuration rules module displays to a user the results of comparison of each of the above principles to the user-entered electron configuration, and optionally suggests modifications to the electron configuration to form a valid configuration.

From the electron configuration rules module 114, operational flow proceeds to an end operation 116, which corresponds to completed analysis of the currently input electron configuration at the configuration rules module 114. Additionally, if the electron configuration check operation is not selected, operational flow branches "no" to the end operation 116.

The end operation 116 does not necessarily refer to completion of execution of software, but rather merely completed analysis of the current electron configuration. Once another electron configuration is entered into a user interface (i.e., into the user electron configuration module 106), other modules could update other user interfaces (e.g., the atomic orbital simulation, alphanumeric representation, electron dot diagram, periodic table, or other user interface components).

The various modules of the flowchart 100 need not necessarily execute in the order described herein. For example, following analysis of a particular electron configuration at the configuration rules module 114, a user could modify the electron configuration (e.g., user electron configuration module 106), thereby causing an update to the display (e.g. operation of display module 108). However, following each new electron configuration input into a user interface and received by the user electron configuration module 106, the display module 108 will execute and update electron configuration diagrams. Other arrangements are possible as well.

Figure 2:
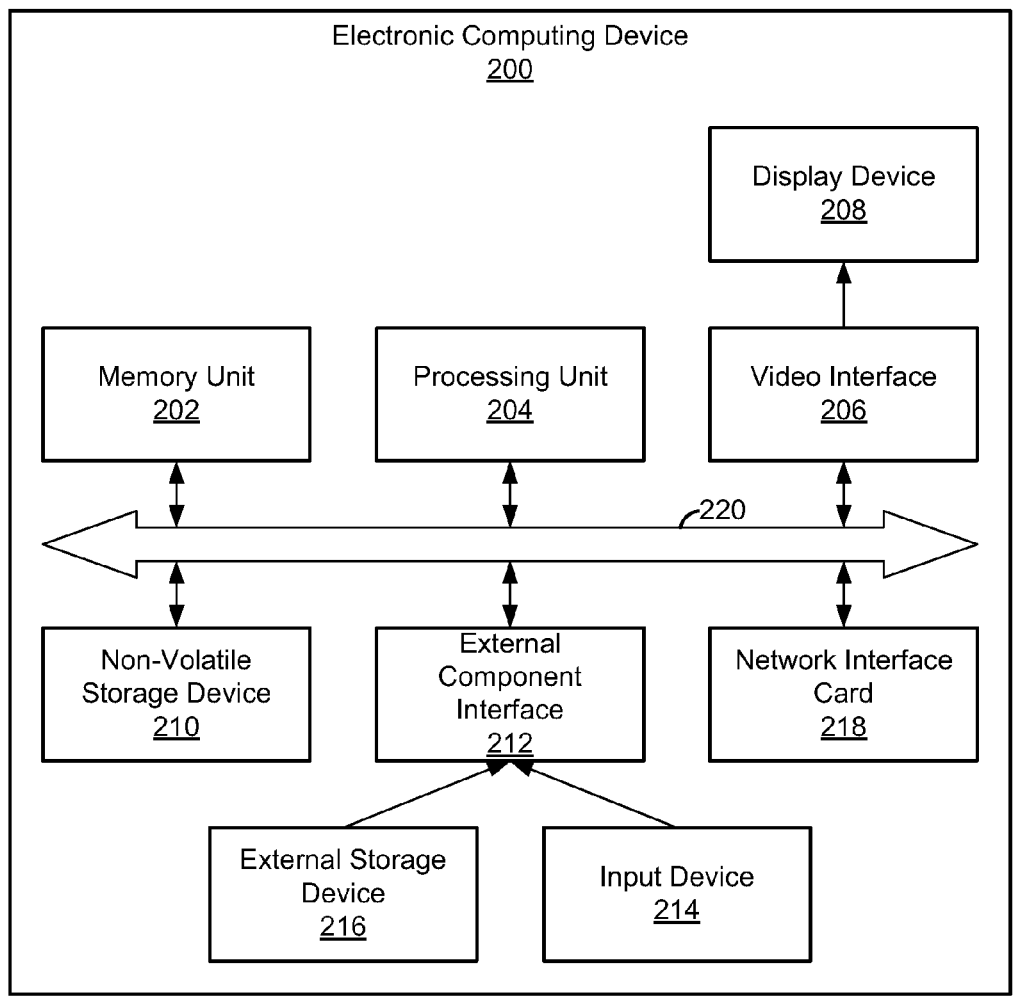
FIG. 2 is a block diagram illustrating example physical components of an electronic computing device useable to implement the various methods and systems described herein.

FIG. 2 is a block diagram illustrating example physical components of an electronic computing device 200, which can be used to execute the various operations described above with respect to FIG. 1. A computing device, such as electronic computing device 200, typically includes at least some form of computer-readable media. Computer readable media can be any available media that can be accessed by the electronic computing device 200. By way of example, and not limitation, computer-readable media might comprise computer storage media and communication media.

As illustrated in the example of FIG. 2, electronic computing device 200 comprises a memory unit 202. Memory unit 202 is a computer-readable data storage medium capable of storing data and/or instructions. Memory unit 202 may be a variety of different types of computer-readable storage media including, but not limited to, dynamic random access memory (DRAM), double data rate synchronous dynamic random access memory (DDR SDRAM), reduced latency DRAM, DDR2 SDRAM, DDR3 SDRAM, Rambus RAM, or other types of computer-readable storage media.

In addition, electronic computing device 200 comprises a processing unit 204. As mentioned above, a processing unit is a set of one or more physical electronic integrated circuits that are capable of executing instructions. In a first example, processing unit 204 may execute software instructions that cause electronic computing device 200 to provide specific functionality. In this first example, processing unit 204 may be implemented as one or more processing cores and/or as one or more separate microprocessors. For instance, in this first example, processing unit 204 may be implemented as one or more Intel Core 2 microprocessors. Processing unit 204 may be capable of executing instructions in an instruction set, such as the x86 instruction set, the POWER instruction set, a RISC instruction set, the SPARC instruction set, the IA-64 instruction set, the MIPS instruction set, or another instruction set. In a second example, processing unit 204 may be implemented as an ASIC that provides specific functionality. In a third example, processing unit 204 may provide specific functionality by using an ASIC and by executing software instructions.

Electronic computing device 200 also comprises a video interface 206. Video interface 206 enables electronic computing device 200 to output video information to a display device 208. Display device 208 may be a variety of different types of display devices. For instance, display device 208 may be a cathode-ray tube display, an LCD display panel, a plasma screen display panel, a touch-sensitive display panel, a LED array, or another type of display device.

In addition, electronic computing device 200 includes a non-volatile storage device 210. Non-volatile storage device 210 is a computer-readable data storage medium that is capable of storing data and/or instructions. Non-volatile storage device 210 may be a variety of different types of non-volatile storage devices. For example, non-volatile storage device 210 may be one or more hard disk drives, magnetic tape drives, CD-ROM drives, DVD-ROM drives, Blu-Ray disc drives, or other types of non-volatile storage devices.

Electronic computing device 200 also includes an external component interface 212 that enables electronic computing device 200 to communicate with external components. As illustrated in the example of FIG. 2, external component interface 212 enables electronic computing device 200 to communicate with an input device 214 and an external storage device 216. In one implementation of electronic computing device 200, external component interface 212 is a Universal Serial Bus (USB) interface.

In other implementations of electronic computing device 200, electronic computing device 200 may include another type of interface that enables electronic computing device 200 to communicate with input devices and/or output devices. For instance, electronic computing device 200 may include a PS/2 interface. Input device 214 may be a variety of different types of devices including, but not limited to, keyboards, mice, trackballs, interactive whiteboards, stylus input devices, touch pads, touch-sensitive display screens, or other types of input devices. External storage device 216 may be a variety of different types of computer-readable data storage media including magnetic tape, flash memory modules, magnetic disk drives, optical disc drives, and other computer-readable data storage media.

In the context of the electronic computing device 200, computer storage media includes volatile and nonvolatile, removable and non-removable media implemented in any method or technology for storage of information such as computer readable instructions, data structures, program modules or other data. Computer storage media includes, but is not limited to, various memory technologies listed above regarding memory unit 202, non-volatile storage device 210, or external storage device 216, as well as other RAM, ROM, EEPROM, flash memory or other memory technology, CD- ROM, digital versatile disks (DVD) or other optical storage, magnetic cassettes, magnetic tape, magnetic disk storage or other magnetic storage devices, or any other medium that can be used to store the desired information and that can be accessed by the electronic computing device 200.

In addition, electronic computing device 200 includes a network interface card 218 that enables electronic computing device 200 to send data to and receive data from an electronic communication network. Network interface card 218 may be a variety of different types of network interface. For example, network interface card 218 may be an Ethernet interface, a token-ring network interface, a fiber optic network interface, a wireless network interface (e.g., WiFi, WiMax, etc.), or another type of network interface.

Electronic computing device 200 also includes a communications medium 220. Communications medium 220 facilitates communication among the various components of electronic computing device 200. Communications medium 220 may comprise one or more different types of communications media including, but not limited to, a PCI bus, a PCI Express bus, an accelerated graphics port (AGP) bus, an Infiniband interconnect, a serial Advanced Technology Attachment (ATA) interconnect, a parallel ATA interconnect, a Fiber Channel interconnect, a USB bus, a Small Computer System Interface (SCSI) interface, or another type of communications medium.

Communication media, such as communications medium 220, typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Example electronic computing device 200 includes several computer-readable data storage media (i.e., memory unit 202, non-volatile storage device 210, and external storage device 216). Together, these computer-readable storage media may constitute a single data storage system. As discussed above, a data storage system is a set of one or more computer-readable data storage mediums. This data storage system may store instructions executable by processing unit 204. Activities described in the above description may result from the execution of the instructions stored on this data storage system. Thus, when this description says that a particular logical module performs a particular activity, such a statement may be interpreted to mean that instructions of the logical module, when executed by processing unit 204, cause electronic computing device 200 to perform the activity. In other words, when this description says that a particular logical module performs a particular activity, a reader may interpret such a statement to mean that the instructions configure electronic computing device 200 such that electronic computing device 200 performs the particular activity.

One of ordinary skill in the art will recognize that additional components, peripheral devices, communications interconnections and similar additional functionality may also be included within the electronic computing device 200 without departing from the spirit and scope of the present disclosure.

In the examples described herein, the electronic computing device 200 executes instructions stored in memory to implement the systems and methods described herein. For example, the electronic computing device 200 can include a program stored in memory. When the electronic computing device 200 executes the program, the electronic computing device 200 creates and/or performs the modules/operations shown in FIG. 1 and renders the user interfaces shown in FIGS. 3-7.

Now referring to FIGS. 3A-3B, user interfaces are illustrated that can be used to display models of atomic orbitals corresponding to various electron configurations.

Figure 7A:
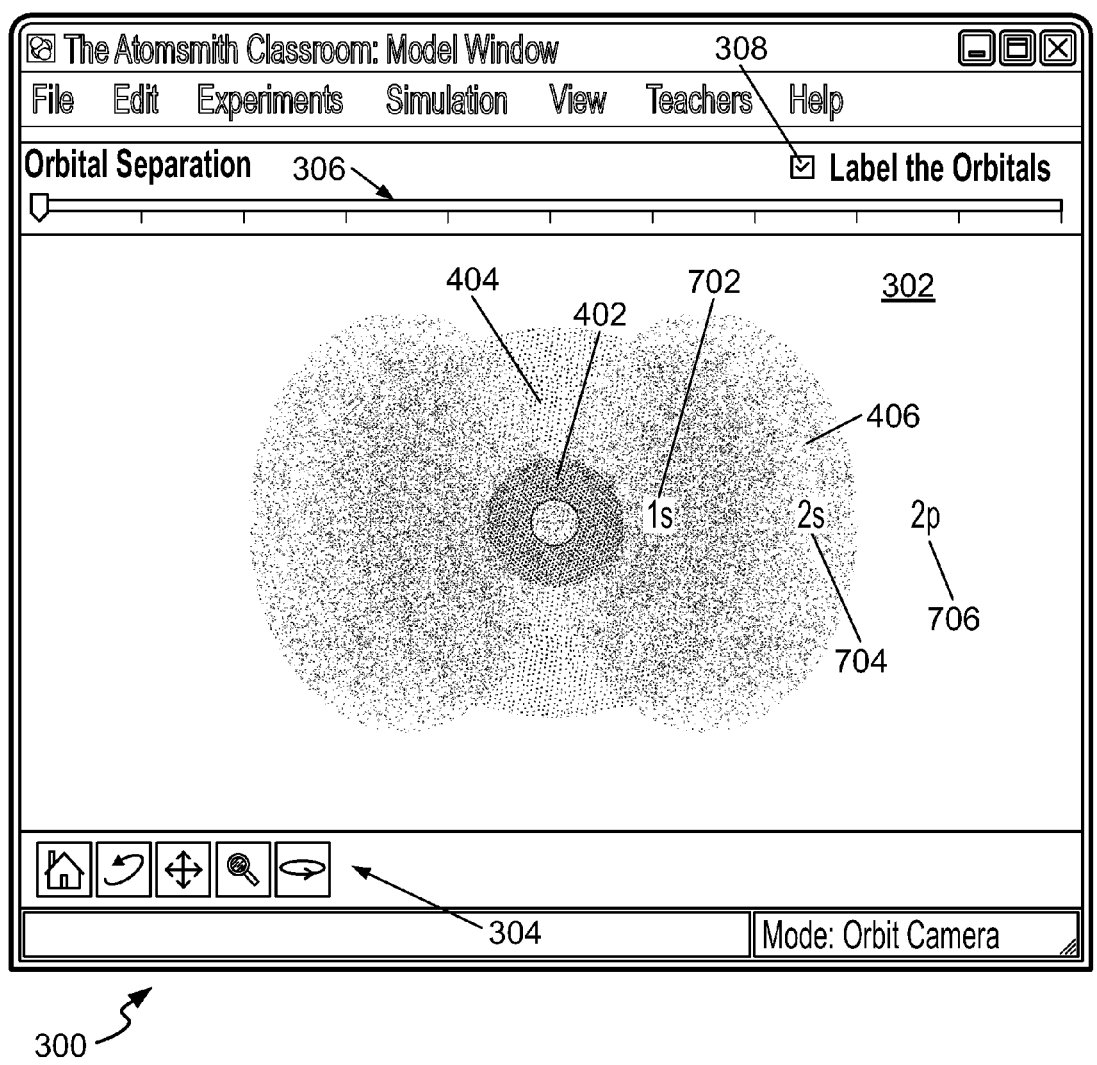
FIG. 7A illustrates an example implementation of the user interface of FIG. 3A displaying the atomic orbital simulation of a beryllium atom.

FIG. 3A illustrates a user interface 300 capable of displaying the three-dimensional electron distribution in an atom. The electron distribution is represented as a "cloud" of small, colored points that represent positions where the electron is most likely to be found. User interface 300 also optionally presents an animation consisting of small spheres moving randomly among these positions of high probability, representing movement of the electron in the atomic orbital. FIG. 3B illustrates a user interface 320 useable for user-manipulation of electron configurations in an atom (an atomic orbital). User interface 300 of FIG. 3A includes a general display area 302 for displaying atomic orbital simulations surrounding a simulated nucleus of an atom. Display modification buttons 304 allow manipulation of the simulations, for example to rotate, pivot, move, zoom or reset the view displayed in area 302. A slider bar 306 allows a user to separate atomic orbitals, thereby isolating each of the orbitals included in the displayed electron configuration (e.g., as shown and described in greater detail in conjunction with FIGS. 7D-7E). Check box 308 allows a user to elect to label the various orbitals included in the electron configuration (e.g., as shown in FIGS. 7A, 7D, and 7E).

User interface 320 includes an orbital box diagram 322, into which a user can enter electron configurations. The orbital box diagram 322 displays the various possible electron shells, or energy levels, and the orbitals into which the electrons can be placed. In the embodiment shown, the 1s, 2s, 2p, 3s, 3p, 4s, 3d, and 4p energy levels and associated orbitals are shown (i.e., a single orbital for each s energy level, three orbitals for each p energy level, and five orbitals for each d energy level). Each orbital includes a pair of electron positions. A user can select any of the boxes included in the orbital box diagram 322, e.g., by clicking on the box in the user interface. In other examples, more or fewer shell levels (n>4 or n<4) can be shown.

In certain embodiments, different numbers of clicks within a single box will change the presence and spin of an electron associated with that box (and associated shell/energy level). For example, in certain embodiments, a first mouse click causes an "up" spin electron to be placed into the box, a second mouse click changes the "up" spin electron to a "down" spin electron. A third mouse click can remove the electron from the box altogether. A clear button 324 allows clearance of each of the boxes in the orbital box diagram 322.

Each time a box is selected in the orbital box diagram 322 to cause addition (or removal) of an electron relating to a particular orbital, the corresponding display area 302 is altered accordingly to reflect the simulated atom as formed by the user. This display of the movement of electrons in the atomic orbital (animation) is based upon a mathematical formula representing the probability of the presence of an electron in any given position within an orbital at a particular time. A stop animation button 326 allows a user to pause the animation and analyze the "cloud" of points that represents the spatial extent of the orbitals occupied by the particular electron configuration.

A check configuration button 328 allows a user to initiate a computer-based check of the validity of the particular electron configuration entered into the orbital box diagram 322 against electron configuration rules (e.g., the Pauli Exclusion Principle, Hund's Rule, and the Aufbau principle). Therefore, selection of the check configuration button 328 corresponds to selection of the "yes" option of the electron configuration check operation 112, thereby leading to the configuration rules module 114, which can generate a user interface displaying those test results.

Additional details regarding the current electron configuration can be included in the user interface 320 as well. For example, an atomic symbol 330 (shown in FIGS. 4B, 5B, 6B, and 7B) denotes the atom having the number of electrons currently selected by the user. Additionally, an electron count 332 includes the number of electrons currently included in the configuration, and an electron configuration listing 334 provides the alphanumeric representation of the electron configuration corresponding to that selected in the orbital box diagram 322.

Operation of the user interfaces of FIGS. 3A-3B are illustrated further in the examples of FIGS. 4-7. FIGS. 4A-4B show user interfaces 300, 320 upon entry of an electron configuration including a single electron in the 1s orbital. Upon entry of the electron in that orbital, a number of additional changes to user interfaces 300, 320 occur. For example, in display area 302 (FIG. 4A), a first atomic orbital 402 is displayed, indicating the presence of an electron in the is orbital. Additionally, in user interface 320 (FIG. 4B), the atomic symbol 330 for hydrogen appears (noted as "H") and a total number of electrons is displayed. Additionally, the alphanumeric representation of the electron configuration 334 is displayed along a bottom edge of the user interface 320 (listed as "$1s^1$").

In addition, within the first atomic orbital 402, a depiction of the electron 403 within the first orbital 402 is provided. In example embodiments, the depiction of the electron 403 within the first orbital 402 is animated to approximate a cloud of random, high-probability positions of the electron 403 within the first orbital 402.

For example, a wave function computation can be used to compute the value of the wave function of the one-electron Schrödinger equation for one atom of a selected element. These values are computed over a three-dimensional region of space surrounding the nucleus of the atom. The square of the wave function value at a given point in space is equal to the probability of finding the electron at that point. Because these calculations can be computationally time-consuming, the wave function values may be "pre-computed" and stored in computer memory or on magnetic (hard disk) storage, and read into program memory as needed. The resulting computations are used to place the electron 403 in likely positions within the first atomic orbital 402 at a given point in time.

Figure 4A:
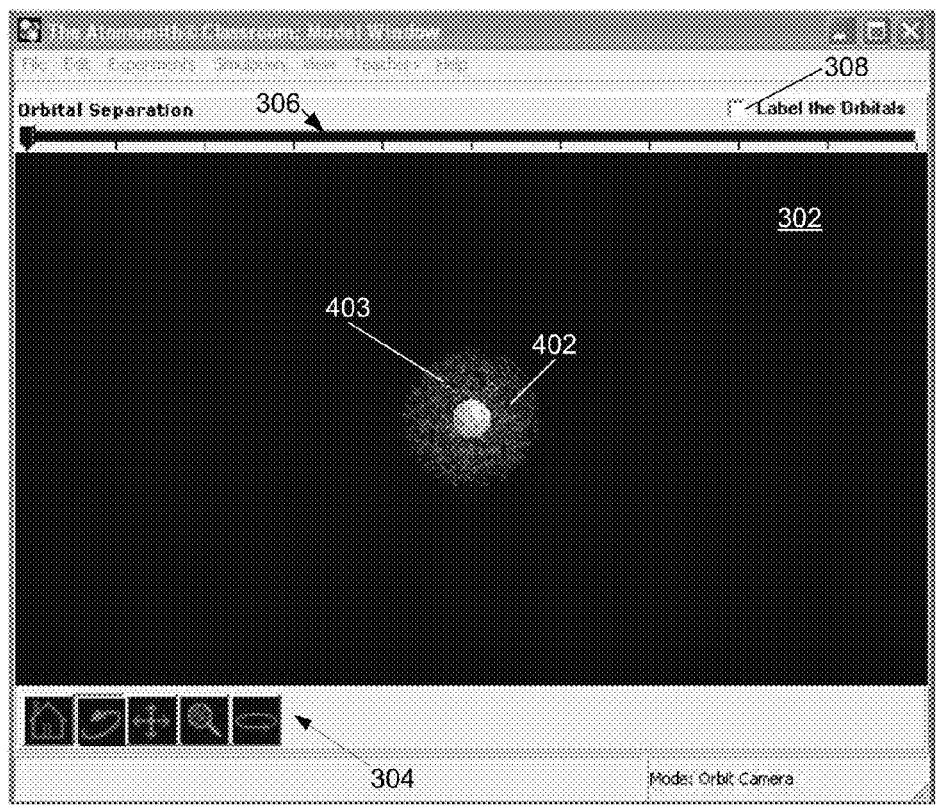
FIG. 4A illustrates an example implementation of the user interface of FIG. 3A displaying the atomic orbital simulation of a hydrogen atom.

Further, in one example, the first atomic orbital 402 is rendered based on logic that reads the values of the electron wave function probabilities from memory and draws a representation of that computed region of three-dimensional space where the electron is likely to be found, within a selected probability. Examples of three-dimensional representations of the atomic orbitals include "clouds" of semi-transparent, colored points, as shown in FIG. 4A. Other three-dimensional structures, such as isosurfaces that represent solids that contain all of the points of a selected probability, can also be used.

When electrons are added to additional orbitals, the electron placement and orbital clouds are calculated and updated in a similar manner. See, for example, FIG. 5A, which shows multiple orbitals 402, 404, 406, 408, and 410.

Figure 4B:
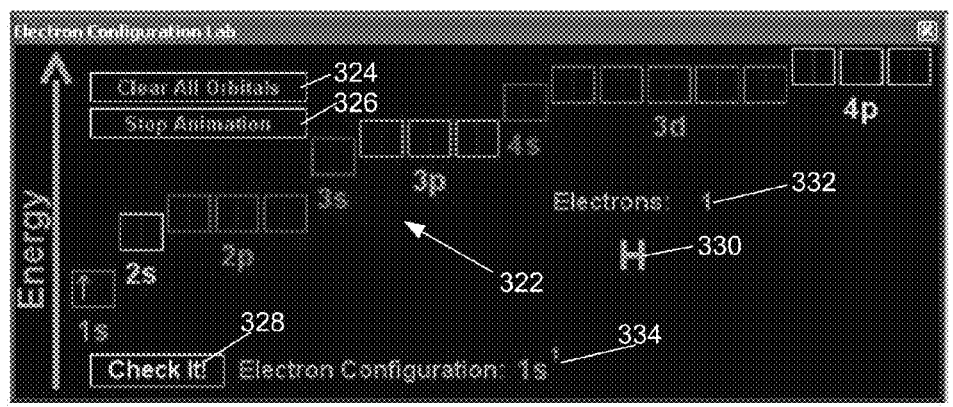
FIG. 4B illustrates an example implementation of the user interface of FIG. 3B to cause the atomic orbital simulation shown in FIG. 4A relating to the hydrogen atom.
Figure 4C:
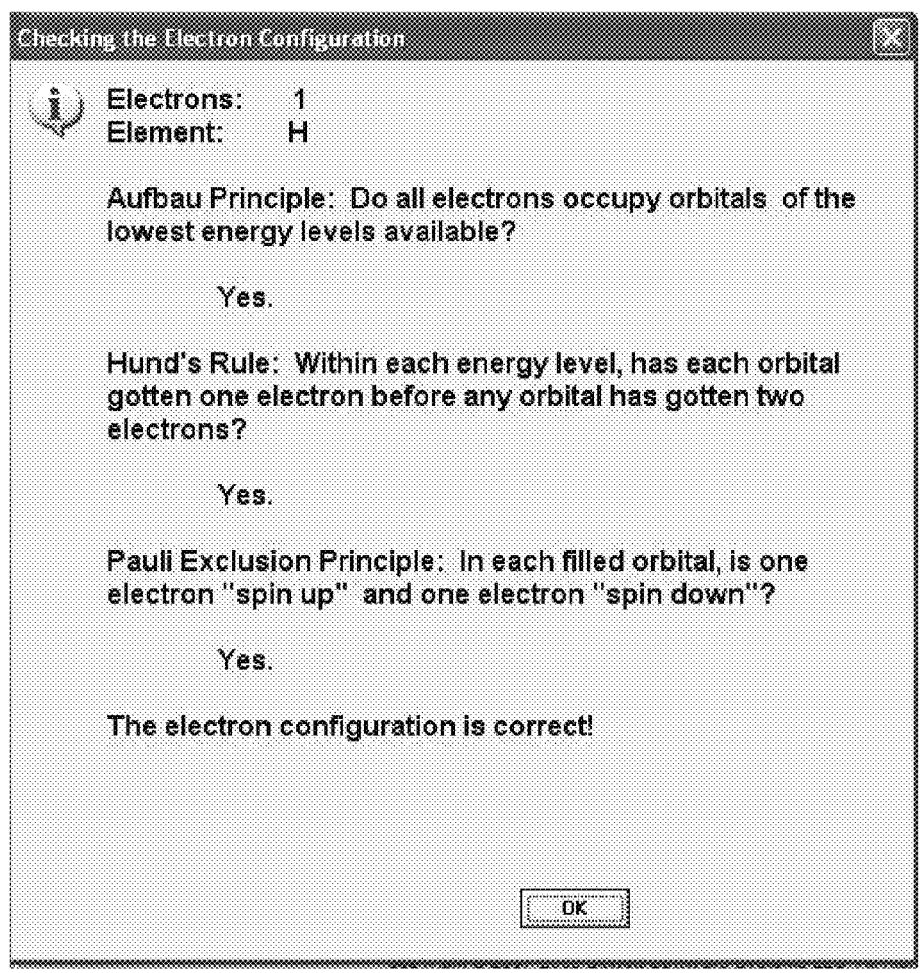
FIG. 4C illustrates an example user interface displaying electron configuration validity status for the electron configuration of FIGS. 4A-4B, according to a possible embodiment of the present disclosure.

FIG. 4C illustrates an example user interface 350 displaying electron configuration validity status for the electron configuration of FIGS. 4A-4B. User interface 350 therefore corresponds to the display of results generated by the configuration rules module 114 of FIG. 1. As shown, user interface 350 displays results of the comparison to electron configuration rules. In the example shown, because a single electron placed in the is orbital is a valid electron configuration for a hydrogen atom, all tests are indicated as passed.

Figure 5A:
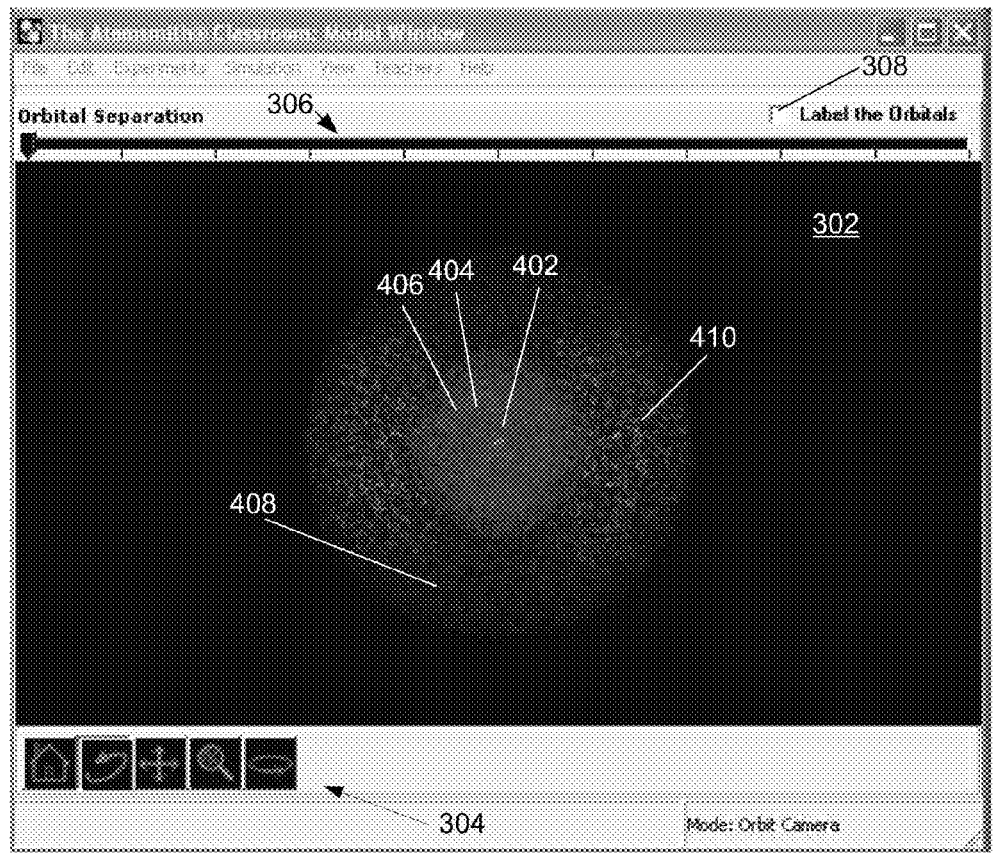
FIG. 5A illustrates an example implementation of the user interface of FIG. 3A displaying the atomic orbital simulation of an aluminum atom.
Figure 5B:
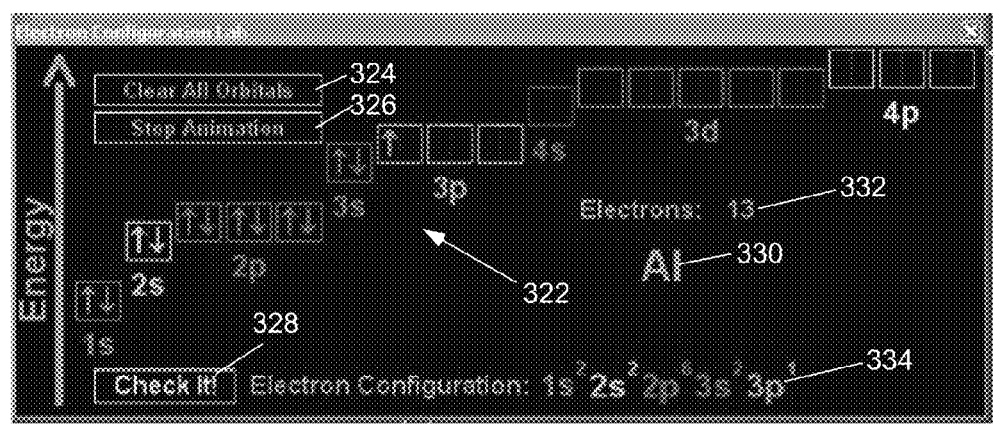
FIG. 5B illustrates an example implementation of the user interface of FIG. 3B to cause the atomic orbital simulation shown in FIG. 5A relating to the aluminum atom.
Figure 5C:
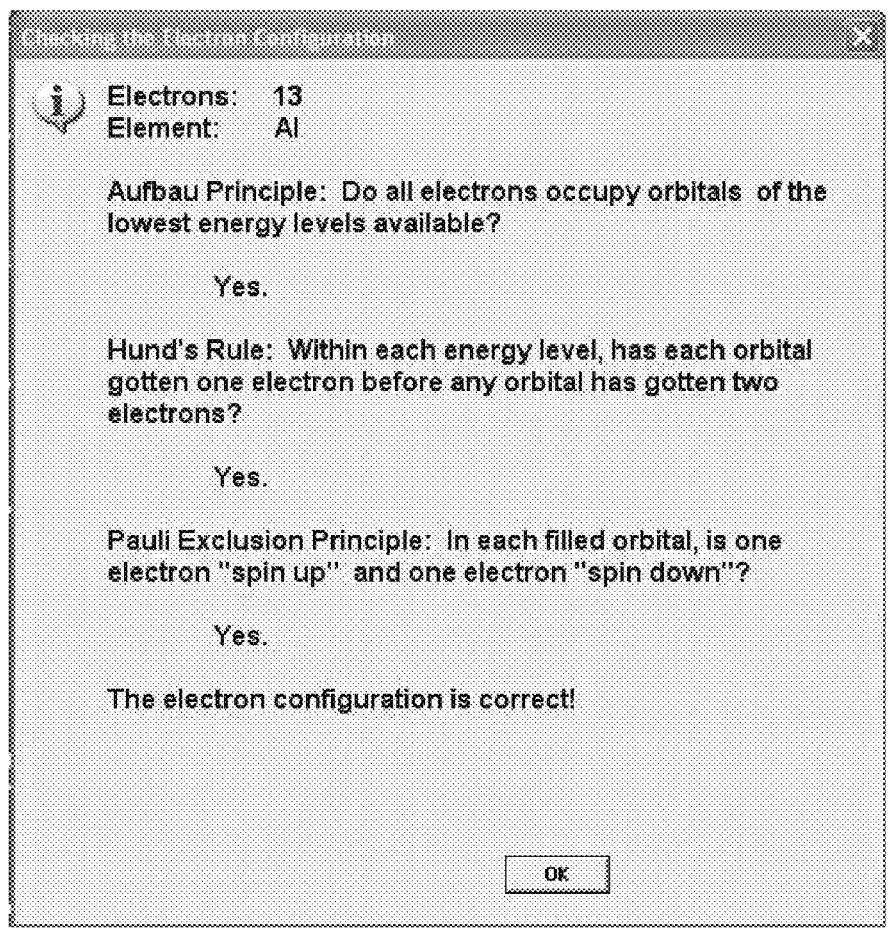
FIG. 5C illustrates an example user interface displaying electron configuration validity status for the electron configuration of FIGS. 5A-5B, according to a possible embodiment of the present disclosure.

FIGS. 5A-5C illustrate a further example of use of the user interfaces 300, 320, 350, in conjunction with a valid aluminum atom. In this case, orbitals 402, 404, 406, 408, and 410 are displayed in display area 302 of FIG. 5A, corresponding to the 1s, 2s, 2p, 3s, and 3p orbitals. The atomic symbol 330 "Al" is shown in user interface 320, and the alphanumeric representation of the electron configuration 334 ($1s^22s^22p^63s^23p^1$) is provided, along with the electron count 332.

FIG. 5C illustrates user interface 350 displaying electron configuration validity status for the electron configuration of FIGS. 5A-5B showing that the electron configuration in orbital box diagram 322 shown in FIG. 5B is a valid configuration for an aluminum atom. Therefore, a user entering this configuration would be deemed to have entered a correct electron configuration, when using a lesson incorporating the methods and systems of the present disclosure.

Figure 6A:
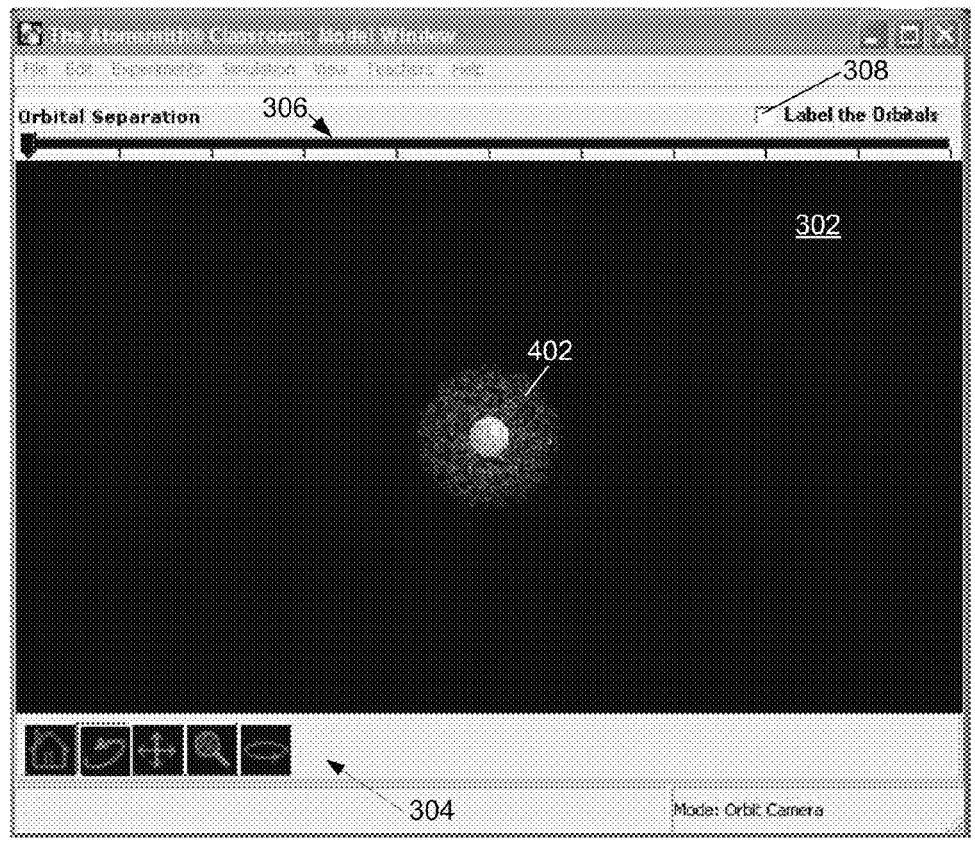
FIG. 6A illustrates an example implementation of the user interface of FIG. 3A displaying the atomic orbital simulation of a helium atom.
Figure 6B:
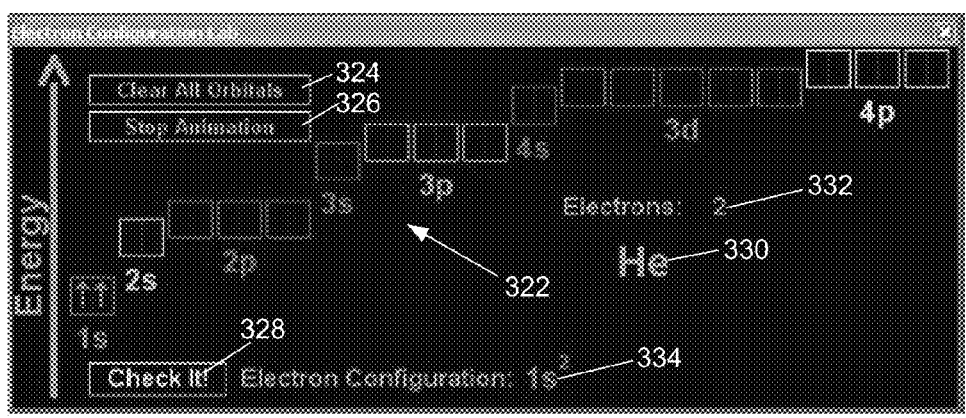
FIG. 6B illustrates an example implementation of the user interface of FIG. 3B to cause the atomic orbital simulation shown in FIG. 6A relating to the helium atom.
Figure 6C:
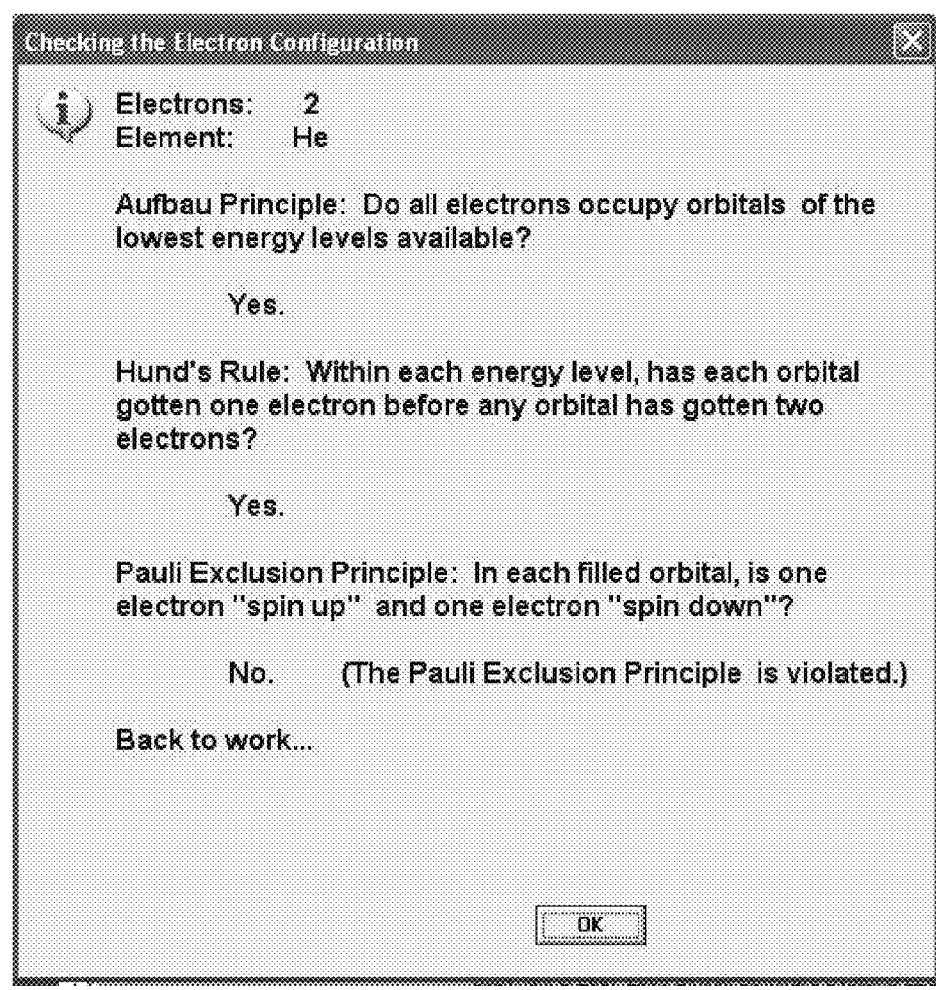
FIG. 6C illustrates an example user interface displaying electron configuration validity status for the electron configuration of FIGS. 6A-6B, according to a possible embodiment of the present disclosure.
Figure 6C:

FIGS. 6A-6C illustrate an example "invalid" electron configuration that violates one or more of the rules evaluated by the configuration rules module 114 of FIG. 1. In the embodiment shown, two electrons are placed in the orbital box diagram in the is orbital 402, but both have "up" spin. The view in display area 302 of this electron configuration appears similar to that shown in FIG. 4A, and the alphanumeric representation of the electron configuration 334 is shown as $1s^2$ (the correct configuration). However, based on the two "up" spinning electrons, the configuration is deemed invalid under the Pauli Exclusion Principle, as shown in user interface 350 as shown in FIG. 6C. Therefore, a student or teacher entering this configuration would be required to correct the configuration prior to being deemed correct in the lesson in which the methods and systems of the present disclosure are incorporated.

Figure 7B:
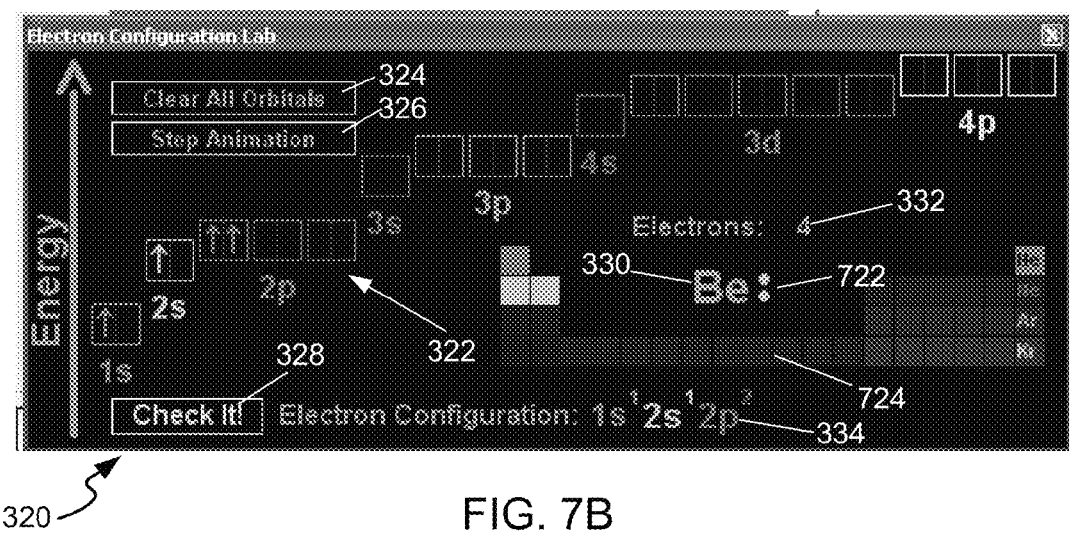
FIG. 7B illustrates an example implementation of the user interface of FIG. 3B, to cause the atomic orbital simulation shown in FIG. 6A relating to the beryllium atom.
Figure 7C:
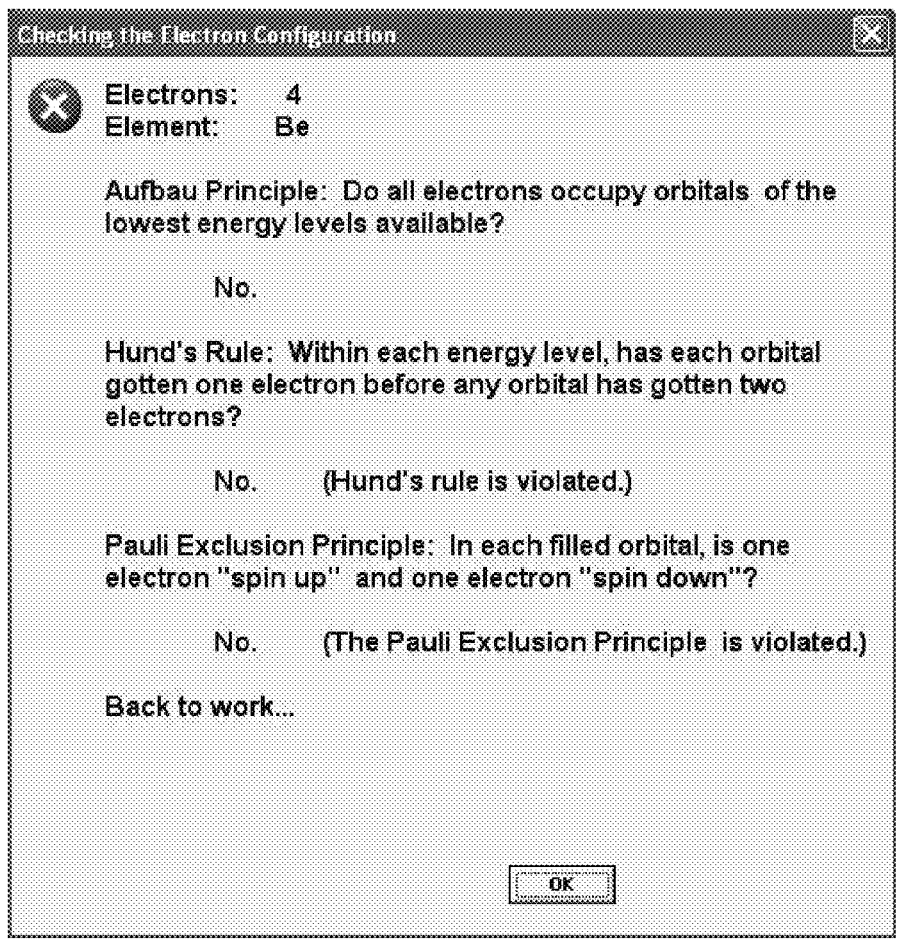
FIG. 7C illustrates an example user interface displaying electron configuration validity status for the electron configuration of FIGS. 7A-7B, according to a possible embodiment of the present disclosure.
Figure 7D:
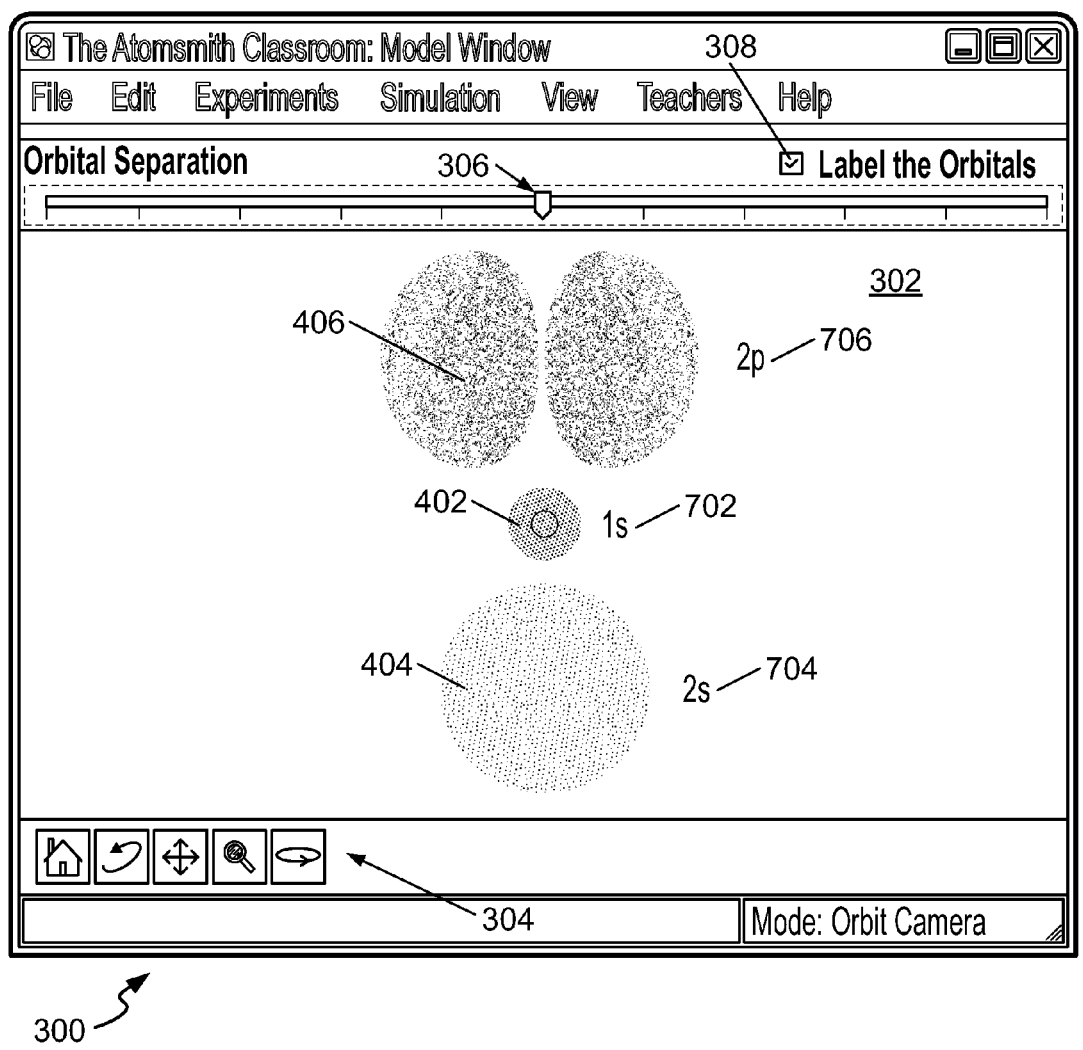
FIG. 7D illustrates the user interface of FIG. 7A after a first user manipulation to label and to separate atomic orbitals.
Figure 7E:
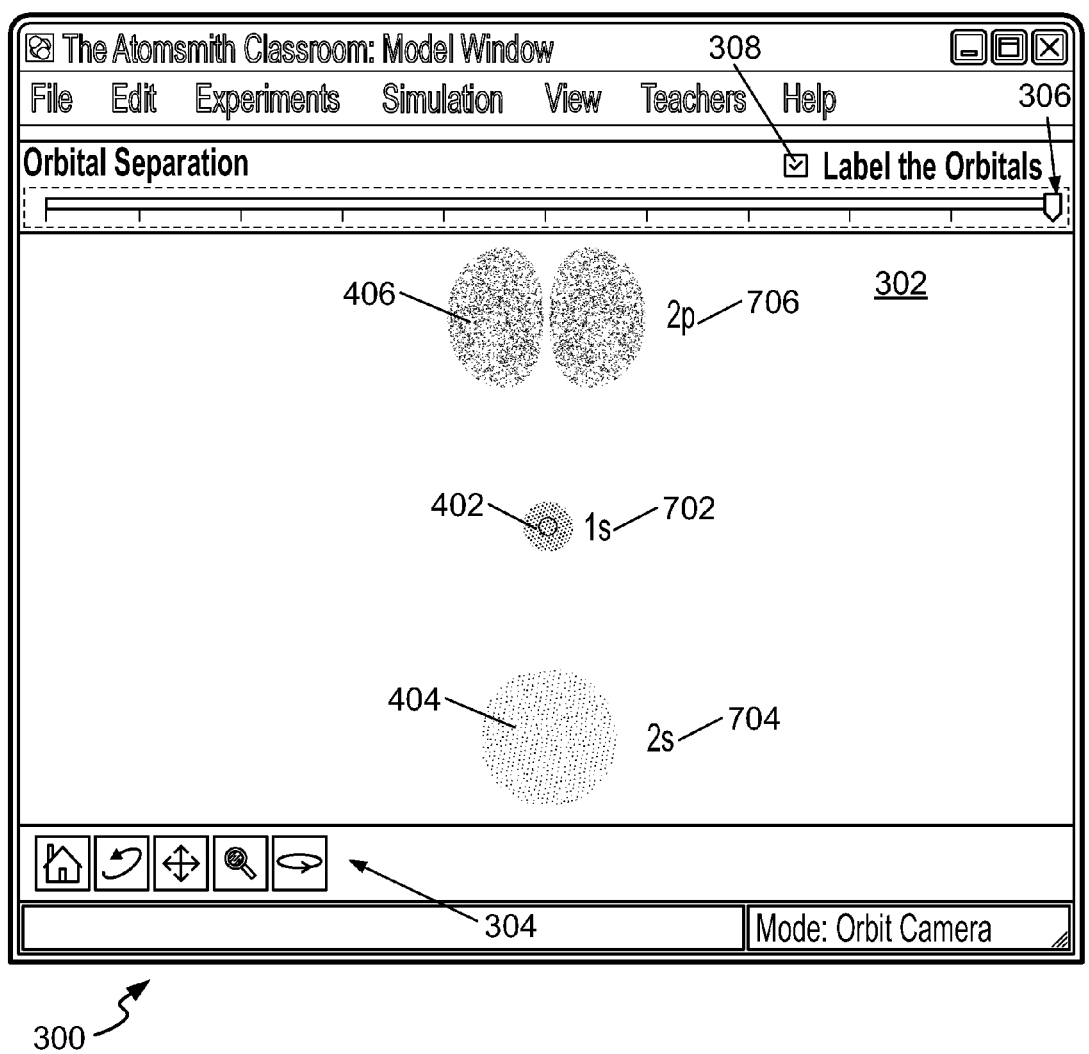
FIG. 7E illustrates the user interface of FIG. 7D after a further user manipulation to separate atomic orbitals.

FIGS. 7A-7E illustrate an example invalid electron configuration of a beryllium atom, and also illustrate certain additional graphical features of the present application that were mentioned briefly in conjunction with FIG. 1, above. FIG. 7A shows user interface 300 displaying an electron configuration of a beryllium atom; FIG. 7B shows user interface 320 with the corresponding entered electron configuration in the orbital box diagram 322. As shown, a user has entered one "up" electron in the 1s orbital, one "up" electron in the 2s orbital, and two "up" electrons in one of the 2p orbitals, therefore representing an overall electron configuration 334 of $1s^12s^12p^2$. These four electrons correspond to the total number of electrons in a beryllium atom, but represent an invalid electron configuration. As illustrated in FIG. 7C, this electron configuration violates all of the Pauli Exclusion Principle, Hund's Rule, and the Aufbau principle.

In FIGS. 7A-7B, certain additional features are shown. In user interface 300, check box 308 is selected, and labels 702, 704, 706 appeared next to the 1s, 2s, and 2p orbitals 402, 404, 406, respectively.

In user interface 320, an electron dot diagram 722 is displayed around the atomic symbol 330 for the atom having the user-entered electron configuration. In the example shown, two dots are displayed on a single side of the "Be" symbol, indicating that two valence electrons exist in a single orbital (in this case, all of the electron configurations rules have been violated, and the two electrons shown at the 2p energy level should first fill the 1s and 2s energy levels, making 2s the valence energy level).

Additionally, a periodic table 724 is displayed. In one example, the periodic table 724 is configured to highlight the currently-configured element within the periodic table. In another example, only a specific sub-set of elements are displayed, such as the noble gases (i.e., He, Ne, Ar, Kr). In one example, the user can click on the noble gases within the periodic table 724, and the orbital box diagram 322 is filled with the electrons corresponding to the selected noble gas and the alphanumeric representation of the electron configuration employs a noble gas "shorthand" notation. In other examples, the user can click on any element in the periodic table 724, and thereupon the orbital box diagram 322 is filled out for that selected element.

In another example, the various elements in the periodic table 724 are highlighted as the user adds electrons to the orbital box diagram 322. For example, if the user adds two electrons to the is orbital, the element helium (He) is highlighted to illustrate to the user that this electron configuration represents He. Other configurations are possible.

FIGS. 7D-7E illustrate stages of operation of slider bar 306 in the user interface 300, separating the 1s, 2s, and 2p orbitals of the beryllium atom as entered (incorrectly) into the orbital box diagram 322 of FIG. 7B. FIG. 7E illustrates orbitals 402, 404, 406 fully separated, with the slider bar 306 positioned to the far right side of the user interface 300. FIG. 7D illustrates orbitals 402, 404, 406 partially separated, as the slider bar 306 is positioned at a midpoint between a default overlapping arrangement (e.g., as shown in FIG. 7A), and a fully separated arrangement (shown in FIG. 7E).

Other configurations for the systems and methods described herein are possible. For example, in one alternative, the orbital box diagram can be replaced with another model used to represent electron configurations, such as a line notation that uses horizontal line segments over which representations of electrons are drawn or circle notation in which representations of electrons are drawn.

In addition, the examples described herein use cloud diagrams to visually represent the atomic orbitals. However, other configurations, such as isosurfaces, can also be used to represent one or more of the orbitals.

In use, the computerized teaching systems and methods of the present disclosure improve the efficiency and ease with which students or other users are taught about and can explore electron configurations in atoms and with which teachers can demonstrate and lecture about electron configuration in atoms. These systems and methods provide interactive feedback to the student regarding valid and invalid electron configurations, improve visualization of the atomic orbital arrangements of various atoms, and improve students' synthesis of the relationships between atomic structure, valence electrons (important in chemical bonding) as depicted in electron dot diagrams, and the periodic table's representation of the relationships between the elements.

The various embodiments described above are provided by way of illustration only and should not be construed to be limiting. Various modifications and changes may be made to the embodiments described above without departing from the true spirit and scope of the disclosure.

What is claimed is:

1. A computerized method of demonstrating electron configurations in an atomic structure, the method comprising:

presenting to a user one or more user interfaces stored in memory of the computing system, the one or more user interfaces including electron configuration diagrams;

receiving user input into an orbital diagram displayed in the one or more user interfaces, the user input defining an electron configuration by placing elements representing electrons within atomic orbitals of the orbital diagram;

allowing the user to define a spin state for each of the elements;

upon specification of the electron configuration, generating, by a computing device, interactive visual representations of probability distributions, in three-dimensional space, of all the atomic orbitals that represent the specified electron configuration;

allowing user input to select between showing all atomic orbitals corresponding to the specified electron configuration in: (i) a visually non-overlapping configuration where all of the specified atomic orbitals are separated in three dimensions, (ii) a visually overlapping configuration where all of the specified atomic orbitals are concentric in three dimensions, and (iii) one or more partially overlapping configurations where all of the specific atomic orbitals are partially concentric in three dimensions; and allowing user input to interactively specify the user's three-dimensional viewpoint of the generated atomic orbitals in both their visually non-overlapping and overlapping configurations.

2. The method of claim 1, wherein the orbital diagram is an orbital box diagram, and the orbital box diagram allows the user to select one or more boxes in the orbital box diagram to add, remove, or change the spin of electrons.

3. The method of claim 1, further comprising modifying the atomic orbitals based on additional user input adding or removing electrons.

4. The method of claim 3, wherein the one or more user interfaces includes an option to label each of the atomic orbitals.

5. The method of claim 3, further comprising, in response to user manipulation, visually overlapping and separating each of the atomic orbitals.

6. The method of claim 1, wherein the electron configuration diagrams include an electron dot diagram.

7. The method of claim 1, wherein the electron configuration diagrams include an alphanumeric representation of the electron configurations or a periodic table.

8. The method of claim 7, wherein, upon selection by the user of one element in the periodic table, the electron configuration diagrams and atomic orbitals associated with the element are displayed.

9. The method of claim 1, further comprising, upon user request, generating a report regarding compliance of the user-entered electron configuration with one or more electron configuration rules.

10. An electron configuration teaching system comprising:

a display;

a memory configured to store a plurality of user interfaces capable of presentation on the display, the plurality of user interfaces including electron configuration diagrams;

a programmable circuit operatively connected to the display and the memory, the programmable circuit configured to execute program instructions to:

present on the display one or more of the user interfaces;

receive user input into an orbital box diagram displayed in the one or more user interfaces, the user input defining a possible electron configuration;

update the one or more user interfaces to illustrate the electron configuration received from the user; and provide a slider bar that allows the user to define a configuration of an electronic configuration diagram;

wherein at least one of the one or more user interfaces displays the electron configuration diagram including all atomic orbitals corresponding to the orbital box diagram; and wherein the slider bar is configured to allow the user to move a slider of the slider bar to show: (i) a visually non-overlapping configuration where all of the specified atomic orbitals are separated in three dimensions, (ii) a visually overlapping configuration where all of the specified atomic orbitals are concentric in three dimensions; and (iii) one or more partially overlapping configurations where all of the specific atomic orbitals are partially concentric in three dimensions.

11. The electron configuration teaching system of claim 10, wherein the electron configuration diagrams include an electron dot diagram.

12. The electron configuration teaching system of claim 10, wherein the electron configuration diagrams include a periodic table.

13. The electron configuration teaching system of claim 10, wherein the programmable circuit is further programmed to generate a report regarding compliance of the user-entered electron configuration with one or more electron configuration rules.

14. The electron configuration teaching system of claim 10, wherein the one or more electron configuration rules are selected from the group consisting of:
the Pauli Exclusion Principle;
Hund's Rule; and
the Aufbau principle.

* * * * *

UNITED STATES PATENT AND TRADEMARK OFFICE
CERTIFICATE OF CORRECTION

PATENT NO. : 8,672,685 B2  Page 1 of 1
APPLICATION NO. : 12/574933
DATED : March 18, 2014
INVENTOR(S) : Doherty It is certified that error appears in the above-identified patent and that said Letters Patent is hereby corrected as shown below:

In the Specification

Col. 4, line 67: "if the is orbital" should read --if the 1s orbital--

Col. 5, line 1: "If the is orbital is full" should read --If the 1s orbital is full--

Col. 9, line 28: "electron in the is" should read --electron in the 1s--

Col. 10, line 8: "placed in the is orbital" should read --placed in the 1s orbital--

Signed and Sealed this
Fourteenth Day of October, 2014

Michelle K. Lee
*Deputy Director of the United States Patent and Trademark Office*